(12) United States Patent
Hall et al.

(10) Patent No.: US 8,475,442 B2
(45) Date of Patent: Jul. 2, 2013

(54) ULTRASONIC ASSEMBLY WITH ADJUSTABLE FLUID LENS

(75) Inventors: Christopher Stephen Hall, Hopewell Junction, NY (US); Anna Teresa Fernandez, Croton-On-Hudson, NY (US); Jan Frederik Suijver, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 622 days.

(21) Appl. No.: 12/663,307

(22) PCT Filed: Jul. 7, 2008

(86) PCT No.: PCT/IB2008/052716
§ 371 (c)(1),
(2), (4) Date: Dec. 7, 2009

(87) PCT Pub. No.: WO2009/007900
PCT Pub. Date: Jan. 15, 2009

(65) Prior Publication Data
US 2010/0185126 A1    Jul. 22, 2010

Related U.S. Application Data

(60) Provisional application No. 60/949,030, filed on Jul. 11, 2007.

(51) Int. Cl.
*A61B 18/04* (2006.01)

(52) U.S. Cl.
USPC ................................. 606/27; 606/28

(58) Field of Classification Search
USPC ...................................... 606/27, 28
See application file for complete search history.

(56) References Cited

U.S. PATENT DOCUMENTS

| | | | |
|---|---|---|---|
| 7,066,895 B2 | 6/2006 | Podany | |
| 7,773,306 B2 * | 8/2010 | Van As et al. | 359/666 |

(Continued)

FOREIGN PATENT DOCUMENTS

| | | |
|---|---|---|
| RU | 2093791 C1 | 10/1997 |
| WO | WO0172373 | 10/2001 |

(Continued)

OTHER PUBLICATIONS

Young J. Yoon et al., "Ultrasonic Phased Arrays With Variable Geometric Focusing for Hyperthermia Applications", IEEE Transactions on Ultrasonics Ferroelectrics and Frequency Control, 39 Mar. 1992, No. 2, New York, US, pp. 273-278.

(Continued)

*Primary Examiner* — Michael Peffley
*Assistant Examiner* — Jocelyn D Ram (57) ABSTRACT

An ultrasonic assembly suited for attachment to a catheter, e.g. for medical treatment. The ultrasonic assembly includes an adjustable ultrasonic focus mechanism arranged in connection with the ultrasonic transducer to adjust focus of ultrasonic waves generated by the transducer. The ultrasonic focus mechanism includes a fluid focus lens with at least two fluids separated by an interface such that ultrasonic waves are substantially reflected at the interface. At least two electrodes are arranged in connection with the fluid focus lens so as to allow adjustment of the interface shape, e.g. a curvature of the interface, when a voltage is applied to the electrodes. In preferred embodiments the electrodes are arranged so as to allow adjustment of the fluid focus lens in an elevation direction as well as in a radial direction. In simple embodiments with rotational symmetric geometry with the transducer positioned in the center of the fluid focus lens, ultrasonic waves can be focused in an annular ring. This is e.g. suitable for ablative or coagulative necrotic treatment of human tissue, e.g. for atrial fibrillation treatment. In some embodiments, the assembly has a number of separate individually adjustable fluid focus lens compartments allowing a more detailed control of the ultrasonic focus pattern.

15 Claims, 5 Drawing Sheets

U.S. PATENT DOCUMENTS

| | | | |
|---|---|---|---|
| 7,957,219 B2 * | 6/2011 | Hall et al. | 367/7 |
| 2006/0058711 A1 | 3/2006 | Harhen et al. | |
| 2006/0151754 A1 | 7/2006 | Choi et al. | |
| 2008/0264716 A1 * | 10/2008 | Kuiper et al. | 181/176 |
| 2010/0076317 A1 * | 3/2010 | Babic et al. | 600/466 |
| 2010/0229648 A1 * | 9/2010 | Suijver et al. | 73/589 |
| 2010/0280390 A1 * | 11/2010 | Hendriks et al. | 600/467 |
| 2010/0290318 A1 * | 11/2010 | Kuiper et al. | 367/150 |

FOREIGN PATENT DOCUMENTS

| | | |
|---|---|---|
| WO | WO03069380 | 8/2003 |
| WO | WO2005122139 | 12/2005 |

OTHER PUBLICATIONS

Neil R. Smith et al., "Fabrication and Demonstration of Electrowetting Liquid Lens Arrays", Journal of Display Technology, vol. 5, No. 11, Nov. 2009, pp. 411-413.

Martin O. Culjat et al., Evaluation of Gallium-Indium Alloy as an Acoustic Couplant for High-Impedance, High-Frequency Applications, Journal Acoustic Society of America, 118 (2), Aug. 2005, p. 571.

* cited by examiner

ULTRASONIC ASSEMBLY WITH ADJUSTABLE FLUID LENS

FIELD OF THE INVENTION

The invention relates to the field of ultrasonic equipment, more specifically the invention relates to the field of ultrasonic equipment for medical therapy purposes.

BACKGROUND OF THE INVENTION

Atrial fibrillation is a condition that affects roughly 2 million people in the US each year. The disease manifests itself through disorganized firing of electrical signals in the atria of the heart and thereby altering the ability of the heart to contract in an efficient manner. The exact etiology of the disease is manifold, but the treatment is usually through intervention to alter the conductive pathways of the heart.

One approach that is in common use today is ablation of the conductive pathways around the pulmonary vein to prevent the disorganized firings. Several approaches have been used for these treatments and include the use of radio-frequency ablation, cryogenic ablation, laser ablation, microwave ablation and high intensity focused ultrasound ablation. In the case of radio-frequency ablation, a catheter is typically inserted into the femoral vein and guided under X-ray fluoroscopy across the septal wall towards the vicinity of the pulmonary veins. The radio-frequency tip of the catheter is then placed against the wall of the heart and activated. The resulting heat is absorbed by the tissue and results in tissue coagulation and scarring thereby reducing the conductive efficiency of the tissue. This is performed at many spatial locations until the necessary tissue is destroyed. A procedure can take up to 8 hours to perform. A similar procedure is currently in use for cryogenic ablation.

The use of ultrasound as an alternative ablation energy source is advantageous for several reasons. The first is that the heating spot is away from the tip of the catheter—this allows for optimizing damage to the correct conductive cells which are not on the inside of the vein but rather on the epicardial surface. By applying heat to the tissue not in contact with the blood pool, one also minimizes the possible complications due to blood clot formation associated with the heating source. Another advantage with incorporating specially designed ultrasonic sources is that multiple locations can be treated at the same time. This dramatically reduces the treatment time from 6-8 hours to 1 to 2 hours, thereby minimizing the amount of time the patient has to be under anesthesia and increasing workflow efficiency. Furthermore, the opening of a hole in the septal wall is no longer required in all cases, as the ultrasonic transducer can have a focus of several centimeters and the absorption of ultrasound by blood is very small.

US 2006/0058711 A1 by ProRhythm, Inc. has proposed a specific solution for a high intensity focused ultrasound device that can be mounted on the end of a catheter. Their device allows the focusing of sound into an annular ring that coincides with the ostium of the pulmonary vein. Through this mechanism, it is possible to simultaneously heat and destroy tissue circumferentially surrounding the vein. The benefit is realized through reduced procedure time. The ProRhythm design is based on a reflective inflatable balloon that results in ultrasound signals reflected in such a way to focus at a specific location in the acoustic field. The drawback to this design is that a separate catheter with a fixed inflatable balloon has to be used depending on the size of the pulmonary vein. This complicates therapy planning, results in variable outcomes, and also introduces both manufacturing and inventory complications.

Another example of an ultrasonic hyperthermia device can be found in the paper "Ultrasonic Phased Arrays with Variable Geometric Focusing for Hyperthermia Applications" by Y. J. Yoon and P. J. Benkeser, IEEE Transactions on Ultrasonics, Ferroelectrics and Frequency Control, Vol. 39, No. 2, March 1992, pp. 273-278. The device described in this paper obtains 3D adjustable ultrasonic focusing by a combination of controlling a volume of liquid (e.g. silicon oil) in a spherical liquid lens, and electronic focusing by controlling electric phases of a linear phased array. In the liquid lens ultrasonic beams are transmitted through the lens boundary and focused in the transmission through the lens boundary. However, the combined use of a phased array and an adjustable liquid lens to obtain 3D focus control makes this ultrasonic device rather complicated.

SUMMARY OF THE INVENTION

It is an object to provide a simple ultrasonic assembly capable of adjusting focus in 3D such as to allow ultrasonic therapy e.g. on pulmonary veins for treating atrial fibrillation, and to allow simple and economic use, one version of the assembly must be capable of fitting different vein sizes.

In a first aspect, the invention provides an ultrasonic assembly arranged for attachment to a distal end of an associated catheter, the ultrasonic assembly including an ultrasonic transducer arranged to generate ultrasonic waves, a fluid focus lens arranged to focus ultrasonic waves from the transducer, the fluid focus lens including a first fluid arranged with an interface to a second fluid so as to provide an substantial ultrasonic reflection at the interface, and first and second electrodes arranged in connection with the fluid focus lens so as to allow adjustment of a shape of the interface upon application of an electric voltage to the first and second electrodes, so as to allow adjustment of an ultrasonic focus point both in a direction defined by an extension of the associated catheter and in a direction perpendicular to the extension of the associated catheter.

By the term 'fluid' is understood a subset of the phases of matter (fluids include liquids, gases, plasmas, gels and, plastic solids), while in the following the term 'liquid' refers to compounds in the liquid state.

By the term 'fluid focus lens' is understood a lens with controllable focus by application of a voltage. Fluid focus technology is e.g. described in WO 2003/069380 by Philips personnel, and in essence this technology allows light, or other rays or waves, to be focused through alterations in physical boundaries of a fluid filled cavity with specific refractive indices. This process is known as electro-wetting, whereby the fluid within the cavity is moved by the application of a voltage across conductive electrodes, thus accomplishing a movement of the surface of the fluid. This change in surface topology allows light to be refracted in such a way to alter the travel path to cause focusing at a desired location. In this invention, the fluid focus lens includes two fluids with an interface between. The fluids are preferably selected such that the interface reflects the majority of ultrasonic energy generated by the ultrasonic transducer. Via the electro-wetting effect, the shape or topology of the interface can be changed and thus the distribution of ultrasonic rays, thereby enabling a variable or adjustable focus point of the ultrasonic waves. In e.g. medical ablation treatment control of the ultrasonic focus point in space is essential due to the concentration of ultrasonic energy at a well-defined location in space where ablation is desired. The high ultrasonic energy concentrations will be damaging to tissue at all other locations and thus the focusing must be under perfect control during treatment.

By 'interface' is understood the limit between the first and second fluids which may be the first and second fluid being in direct contact, or the interface may include a suitable membrane separating the first and second fluids.

An ultrasonic assembly according to the first aspect is advantageous e.g. for ultrasonic therapy systems, such as for performing ultrasonic therapy on (the vicinity of) the pulmonary veins with the purpose of treating atrial fibrillation. Due to the adjustable fluid interface shape, the ultrasonic focus point can be adjusted in two perpendicular directions, and thus provide ultrasonic focusing controllable in three dimensions (3D). E.g. this can be made possible with embodiments with rotational symmetric focus lenses, where the fluid interface can be controlled such that ultrasonic focus point can be controlled both in a radial direction, i.e. in a direction perpendicular to the extension of the catheter axis, as well as in an elevation direction, i.e. in a direction along the extension of catheter. With such control of the ultrasonic focus point, full control of an ultrasonic therapy is possible, and it is possible to adjust the focus point at a considerable distance from an outer surface of the ultrasonic assembly. Thereby, it is possible that one size of the ultrasonic assembly can be used for treatment of pulmonary veins of different size, or in general treatment of ducts of different size, thus eliminating the need for a large range of assembly sizes to fit a specific patient.

Further, since the electric control circuit necessary to control the geometry of the fluid focus lens is rather simple, and the control can be designed such that only low voltages are involved, e.g. in the order of 10 V, such as 50-80 V. Thus, it is possible to use the assembly in ultrasonic therapy systems that can be implemented with low cost components. Still further, due to the precise 3D focus point control, the assembly enables shorter ultrasonic treatment periods, thus providing increased patient comfort as well as higher patient throughput with the same medical service personnel available. In atrial fibrillation therapy, the assembly also allows adjustment of the depth of field and position of the focus of the deposition of the ultrasonic energy to improve the alteration of the conduction pathways.

Still further, the ultrasonic assembly is advantageous for medical applications, since it can be implemented with first and second fluids that are non-toxic to the human body, and thus no serious harm is caused in case some fluid should accidentally leak when introduced in the human body. E.g. perfluorocarbons and water can be used as fluids for the fluid lens, since these fluids can both satisfy the technical and safety requirements.

The ultrasonic assembly according to the invention is advantageous for all minimally invasive (e.g. catheter-based) high intensity focused ultrasound applications such as in the treatment of atrial fibrillation; potential uses for intravenous or intra-arterial clot dissolution; potential uses for plaque destruction or annealing. Some embodiments may also be used for intra-urinary tract prostate ablation.

In preferred embodiments, the assembly has a substantially rotational symmetric shape with the ultrasonic transducer placed in the centre. Such embodiments enable ultrasonic focus to occur in an annular ring around the centre of assembly, thus making the assembly useful for therapy of a vein which normally has a substantially circular cross section. Still, the annular ring shaped focus point can be obtained with a simple fluid focus lens with only one set of electrodes, and thus electrical control of such embodiment is simple.

In one embodiment, the interface has a substantially spherical shape, or at least the interface has a spherically shaped portion, and wherein the first and second electrodes are arranged so as to allow adjustment of a curvature of the interface.

The ultrasonic transducer may be arranged to generate ultrasonic waves in a radial pattern, thus enabling e.g. treatment of the whole circumference of a pulmonary vein with one position of the ultrasonic assembly. Especially, the first fluid of the fluid focus lens has a rotationally symmetric shape around an axis, wherein the ultrasonic transducer is positioned on the axis in contact with the first fluid, and wherein the interface to the second fluid is adjustable in its curvature, so as to allow a focused ultrasonic beam in a substantially annular ring centered around the axis. Especially, the first fluid provides a meniscus shape, wherein the interface has an adjustable spherical shape. By 'meniscus shape' is understood a body with one convex and one concave side, wherein curvatures of both sides are equal. It is to be understood that meniscus shape is only meant as an example. Alternative shapes may be a body with two major outer surfaces being a substantially flat surface and a substantially ellipsoidal surface etc. Especially, the shape may be a pinned meniscus shape, i.e. a meniscus shape where at least part of the concave surface is replaced by a substantially flat or linear surface.

In preferred embodiments, the ultrasonic transducer is arranged in connection with the first fluid, and wherein the first fluid provides an acoustic window where ultrasonic waves can exit the ultrasonic assembly. The assembly may further include a membrane arranged to at least cover the acoustic window of the first fluid, the membrane being made of a material allowing transmission of ultrasonic waves, preferably with as little absorption of ultrasonic energy as possible. Thus, such material should have an acoustic impedance close to the medium surrounding the assembly, e.g. blood, or have a thickness being half a wavelength of the ultrasonic signal used.

The first and second fluids may be selected such that they are immiscible, and wherein the first and second fluids are in direct contact at the interface. However, the interface between the first and second fluids may also include a flexible membrane. Especially, such membrane can be made of a material being one of: Mylar, Santoprene, Methylpentene copolymer, and natural rubber. The membrane is preferably impermeable and exhibits an acoustic impedance in the range 0.5-5 MRayl, more preferably in the range 1-2 MRayl.

In a class of embodiments, the assembly includes a plurality of fluid focus lens compartments each including respective first and second fluids separated by an interface, and wherein at least two electrodes are arranged to allow individual shape adjustment of the interfaces. This class of embodiments enables angular control of the focus point. Especially, the plurality of fluid focus lens departments may be adjustable so as to allow a focused ultrasonic beam in an annular ring with a centre away from the axis. In some embodiments of this class of embodiments, the plurality of fluid focus lenses compartments are arranged together to form a body with a rotational symmetric shape around an axis. The plurality of focus lens compartments may all have the same shape, or they may have different shapes. It is appreciated that depending on the desired focus point shape, many different configurations of a plurality of fluid focus lens compartments are possible. The number of fluid focus lens compartments may be 2, 3, 4, 5, 6, 7, 8, 9, 10 or even more in case complex focus point shapes are desired.

The first fluid preferably has a low acoustic impedance, such as water or oil. As mentioned, the second fluid preferably serves to provide an interface to the first fluid resulting in a substantial ultrasonic reflection. Thus, the second fluid may be such as air, mercury, or a gallium-indium alloy.

One of the first and second fluids may be chosen to be a substantially non-conducting fluid, while the other one of the first and second fluids is an electrically conducting fluid.

The ultrasonic transducer may be arranged to generate ultrasound power allowing ablative or coagulative necrotic treatment of human tissue. However, for other applications, the ultrasonic transducer may provide an ultrasonic power higher or lower than that suitable for hyperthermia treatment.

In a second aspect, the invention provides an ultrasonic ablation device including a catheter arranged for attachment to an ultrasonic assembly according to the first aspect. The ultrasonic assembly may be mounted fixed to the catheter, or the ultrasonic assembly may be detachable and electrically connected to electric conductors in the catheter by means of an electric connector allowing electric connection to the transducer and the fluid focus lens(es) through the catheter.

Especially, the device is advantageous in sizes suited to be inserted into close proximity to a desired location within a pulmonary vein.

In a third aspect, the invention provides an ultrasonic ablation system including an ultrasonic ablation device according to the second aspect, and a focus control unit electrically connected to the first and second electrodes of the ultrasonic assembly.

It is appreciated that embodiments and advantages mentioned for the first aspect apply as well for the second and third aspects. Further, it is appreciated that the aspects may be combined in any way.

BRIEF DESCRIPTION OF THE DRAWINGS

Embodiments of the invention will be described, by way of example only, with reference to the drawings, in which FIG. 2 illustrates top view (FIG. 2a) and side view (FIG. 2b) of an ultrasonic assembly embodiment, FIG. 6 illustrates a centered position of the assembly in a vein (FIG. 6a) and an off-centre position of the assembly in a vein (FIG. 6b) where an axially symmetric focus is still desired, FIG. 7 illustrates top view (FIG. 7a) and side view (FIG. 7b) of an embodiment where the fluid lens includes six individually controllable fluid lens compartments which enable angularly dependent focus.

DETAILED DESCRIPTION OF EMBODIMENTS

Figure 1:
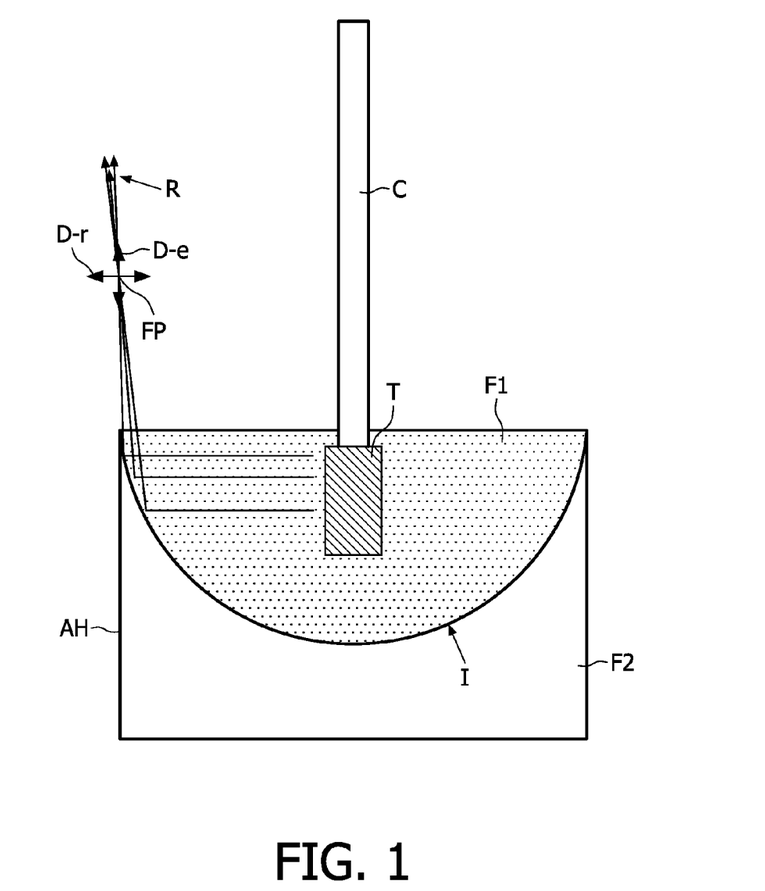
FIG. 1 illustrates an ultrasonic assembly embodiment mounted in a catheter.
Figure 2:
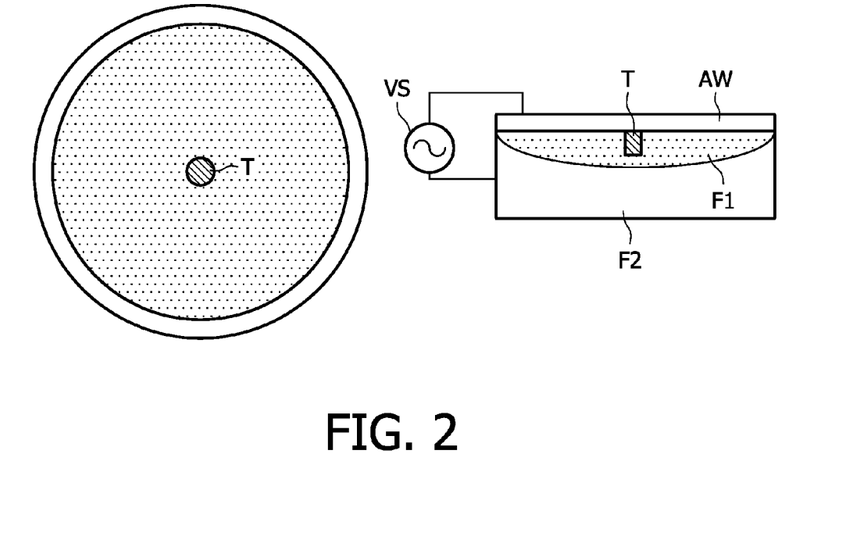

FIGS. 1 and 2 illustrate basic parts of a rather simple ultrasonic assembly embodiment such as for use in medical treatment, e.g. for insertion into human pulmonary veins. FIG. 1 illustrates a side view, while FIG. 2 illustrate a top view (to the left) seen from the catheter C side, and a side view illustrating a voltage source VS connected to control the single fluid focus lens in this embodiment.

In FIG. 1 the ultrasonic assembly embodiment is mounted on a catheter C such as for use in medical treatment. Electrical connections to the transducer and control signal(s) to control the fluid focus lens can be applied from outside via wires inside the catheter C. In the illustrated embodiment, the fluid focus lens formed by a first fluid F1 and a second fluid F2 arranged with an interface I between, has a shape being rotational symmetric around an axis formed by the extension of the catheter C. From FIG. 2 this is seen in the sketch to the left as a circular top section view with the transducer T in the centre of the fluid focus lens. The transducer T is positioned in contact with the first fluid F1, and ultrasonic waves generated by the transducer T are thus transmitted through the first fluid F1 and substantially reflected at the interface I between the first and second fluids F1, F2. FIG. 1 illustrates an assembly housing AH surrounding at least F2.

The interface I has a substantially spherical shape, while the acoustic window AW where ultrasonic waves leave the assembly, forms a substantially plane surface perpendicular to the axis formed by the catheter C. The transducer T is cylindrically symmetric and generating ultrasonic rays, e.g. in the frequency range 1-40 MHz, in a manner perpendicular to the axis of symmetry of the fluid focus lens. Since the transducer is axially symmetric with the interface I, the same curvature is encountered by the ultrasonic rays in all propagation directions. As illustrated, parallel ultrasonic rays R generated from the transducer T radiate through F1, reflect at the interface I and leave the assembly as a bunch of non-parallel rays R intersecting in a focus point FP. Due to the rotation symmetry, the focus point in three dimensions, will form an annular ring circularly symmetric with the transducer. Due to the adjustable shape of the interface I, the radius of this focus point annular ring can be adjusted and also the position of the annular ring in relation to the assembly can be adjusted. In general, the focus point FP can be adjusted in a direction D-e along an axis (a direction which can also be called "elevation") defined by the catheter C as well as in a direction D-r perpendicular to the axis defined by the catheter C (i.e. in a direction which can also be called "radial" direction due to the rotational symmetric shape).

The interface I may include a thin membrane to separate the first and second fluids F1, F2, or the two fluids F1, F2 may be separated due to surface tension, e.g. by one of the fluids being polar while the other one is non-polar.

In FIG. 2b, a voltage source VS applies a DC voltage to the fluid focus lens via first and second electrodes (not expressly illustrated) positioned in connection with the fluid focus lens with the purpose of utilizing the so-called electro-wetting effect to adjust the shape, or more specifically, the curvature of the interface I as a function of the applied voltage. In one embodiment, the first fluid F1 is electrically non-conducting, while the second fluid F2 is electrically conducting. A first electrode is in direct contact with the conducting second fluid F2, while the second electrode, e.g. of cylindrical shape, is electrically isolated with a thin layer. For further general information regarding fluid focus lenses, reference is made to [Appl. Phys. Lett., Vol. 85, page 1128, 2004, by Kuiper and Hendriks.

In embodiments intended for medical treatment, the first fluid F1 is water or oil, i.e. a fluid with acoustic impedances matching human tissue of 1.5 MRayls. The second fluid F2 could be chosen from the below Table where such traits as reflection coefficient (with respect to a 1.5 MRayls interface), ease of handling, biocompatibility, etc. would be considered.

| Material | Density (g/cm3) | Speed of Sound (m/s) | Impedance (MRayl) | Reflection coefficient (%) |
|---|---|---|---|---|
| Air | .001 | 300 | .0003 | 99.9 |
| Mercury | 13.5 | 1450 | 19.6 | 73.5 |
| Ga—In Alloy | 6.4 | 2750 | 17.6 | 71 |

Maximizing the impedance mismatch obviously results in the best reflection coefficient. Mercury has known cyto-toxic effects; however, there are high impedance materials with minimal toxic effects such as Ga—In alloys, see e.g. [Culjat et al.: Acoustics Research Letters Online, Evaluation of gallium-indium alloy as an acoustic couplant for high-impedance, high-frequency applications, Published Online 10 Jun. 2005].

Figure 3:
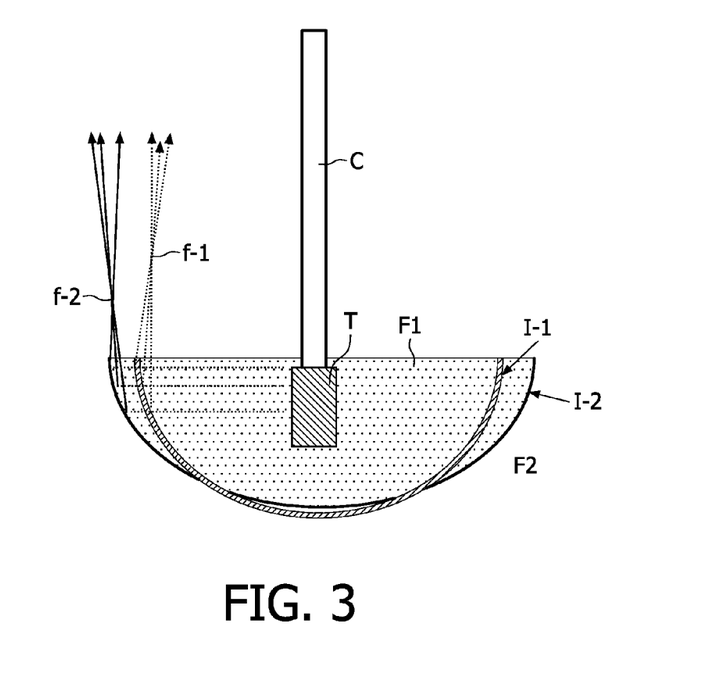
FIG. 3 illustrates focus adjustment by change in fluid interface curvature.

FIG. 3 serves to illustrate on an ultrasonic assembly embodiment similar to that of FIG. 1, a change in the interface between the first fluid F1 and the second fluid F2 caused by application of a voltage as illustrated in FIG. 2b. In one state of the fluid focus lens, e.g, with application of a first voltage, the interface has a first shape I-1, resulting in ultrasonic waves generated by the transducer T being reflected and intersect in a first focus point f-1. Upon application of a second voltage, e.g, in a "relaxed state" of the fluid focus lens without application of a voltage, the interface has a second shape I-2 resulting in a second focus point f-2 which is different from f-1 with respect to radial direction as well as elevation direction.

Figure 4:
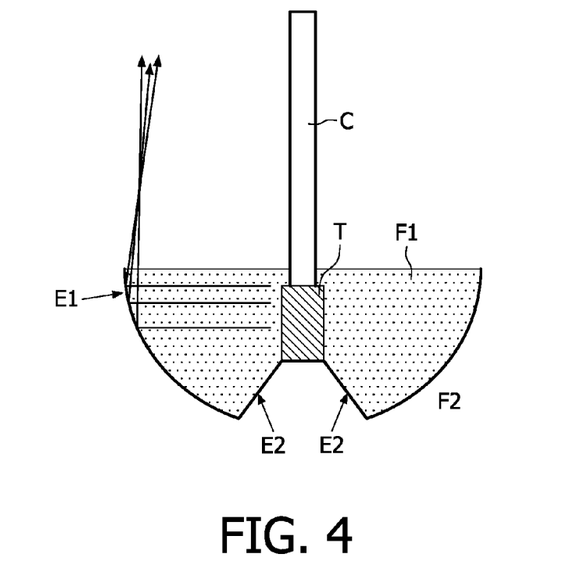
FIG. 4 illustrates an alternative shape of the fluid lens.

FIG. 4 illustrates an alternative ultrasonic assembly with a substantially rotational symmetric fluid focus lens but with a different cross section than those illustrated in FIGS. 1-3. In FIG. 4 it is seen that the first fluid F1 and second fluid F2 provide an interface with a substantially spherical shape in at least a part, similar to the embodiments in FIGS. 1-3, while in the bottom, there is a conical cut in the first fluid boundary, such that the interface has what can be denoted a meniscus shape. Thus, the interface is meniscus shaped in an axially symmetric but non-spherical manner. In this case, the curvature of the lens can vary between curved and flat which may allow a greater range of focuses to occur. Electrodes E1 and E2 are arranged to adjust the shape of the interface between the first and second fluids F1, F2, such that a first electrode E1 is positioned in an upper part of the fluid focus lens, in the spherical part, while a second electrode E2 is positioned in a lower part, the non-spherical part, of the fluid focus lens.

Figure 5:
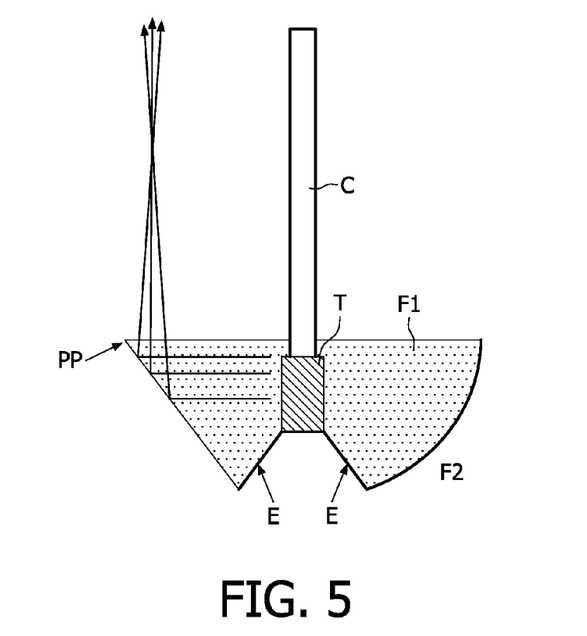
FIG. 5 illustrates another alternative shape of the fluid lens.

FIG. 5 illustrates yet another embodiment with a fluid focus lens with a shape that can be denoted a pinned meniscus. A pinned meniscus is attached to a fixed point, a pinning point PP and then the radius of curvature can be changed without it moving from that pinning point PP. With the pinned meniscus, the interface between the first and second fluids F1, F2 forms a substantially linear or flat part where the reflection of the ultrasonic rays takes place. One or more electrodes E arranged to adjust the interface shape is/are positioned in the lower part of the pinned meniscus. In the illustrated embodiment of FIG. 5, the fluid lens is not rotational symmetric. However, it is to be understood that the pinned meniscus shape with the substantially linear or flat part, where the reflection of the ultrasonic rays takes place, may be formed rotational symmetric.

Rotational symmetric embodiments are suited for ablation applications in veins that are normally substantially circular in cross section.

Figure 6A:
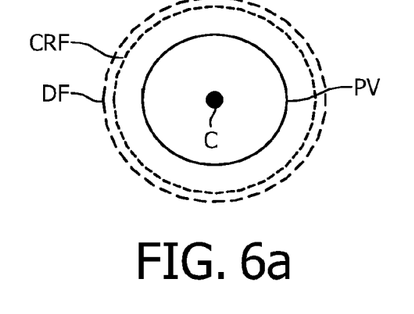

FIG. 6 illustrates, however, a problem with treating a circular vein using an ultrasonic assembly which can provide only a focus point forming a substantially annular ring centered around its catheter axis, in case of an ultrasonic assembly having a size which is considerably smaller than the size of a vein in which it is inserted. In FIG. 6a, a cross sectional view of an ultrasound assembly centered in a pulmonary vein PV is illustrated with catheter C of the assembly in the centre of the pulmonary vein PV. A desired focus DF is illustrated with a dashed line, while a constant radius focus CRF is illustrated with another dashed line. With a rotational symmetric ultrasonic assembly placed in the centre of the pulmonary vein, the assembly will generate ultrasonic waves with an adjustable constant radius focus, and thus it is possible to adjust the focus point to match the desired focus DF.

Figure 6B:
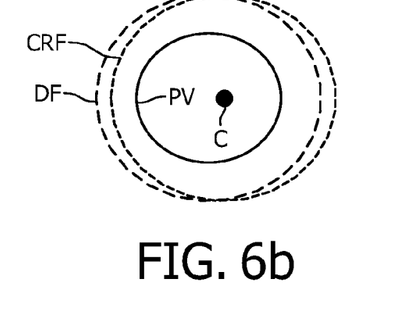

In FIG. 6b, a rotational symmetric assembly is positioned off the centre of the pulmonary vein. Thus, the desired focus point is circular in shape but circular with respect to the vein centre, and thus displaced in relation to the centre of the assembly. Thus, a rotation symmetric assembly as illustrated in FIGS. 1-4 can not be adjusted to comply with the desired focus DF in such situation. Since it is advantageous to have a one-size assembly covering a wide range of vein sizes, the scenario of FIG. 6b is likely to happen.

Figure 7A:
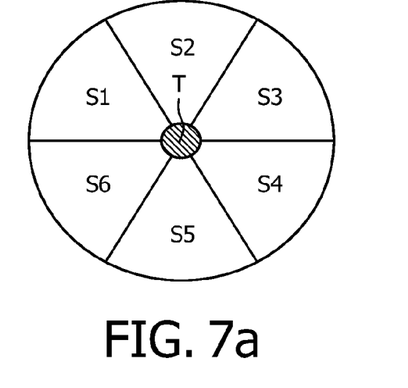
Figure 7B:
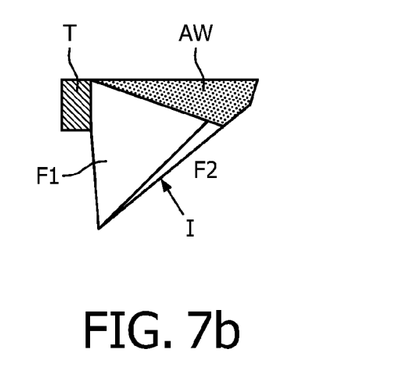

FIG. 7 illustrates a class of ultrasonic assembly embodiments capable of providing a non-rotational symmetric focus point, and thus such embodiments can solve the problem illustrated in FIG. 6. In FIG. 7a, a top view of the assembly is illustrated. The overall assembly shape is substantially circular in top view, but it includes a plurality of separate compartments S1-S6 of the first fluid F1 with the transducer placed in the centre. A cross sectional view of one such compartment is seen to in FIG. 7b with first and second fluids F1, F2 and an adjustable interface I between them and an acoustic window AW where ultrasound rays leave the compartment. It is understood that the ultrasound reflecting interface I can be shaped different from the substantially flat or linear interface I shape sketched, such as also described for the above embodiments. The only requirement is that the interface I must be adjustable in shape such that a desired focus point range adjustment can be obtained.

The basic function of the embodiment of FIG. 7 is similar to what is described for FIGS. 1-5, except that each compartment S1-S6 forms separately adjustable fluid focus lenses. Thus, with separately positioned electrodes and separate control voltages, it is possible to provide proper control of the ultrasonic focus behavior of all of the compartments S1-S6 so as to provide a desired angular focus point shape wherever this is a rotational symmetric shape or a non-rotational symmetric shape.

The embodiment of FIG. 7 provides an angular splitting of ultrasonic rays generated by the transducer T, and these separate angular portions of rays can then be individually focused by the respective individually adjustable lenses or lens compartments S1-S6. Hereby, a desired angular focus pattern can be obtained.

Thus, even though the class of embodiments illustrated in FIG. 7 are more complicated with respect to mechanical construction as well as with respect to electric control, such embodiments are flexible in use and they are suited for one-size manufacturing and still capable of treatment of all sizes of veins.

Figure 8:
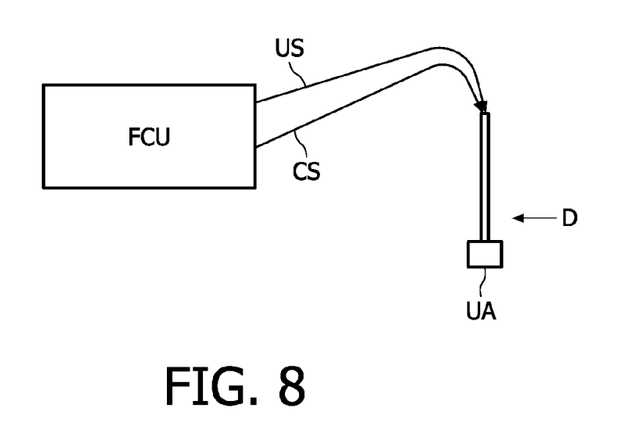
FIG. 8 illustrates an ultrasonic ablation system including a device with an ultrasonic assembly according to the invention.

FIG. 8 sketches basic parts of an ultrasonic ablation system including a focus control unit FCU connected via wires to an ultrasonic device D including an ultrasonic assembly UA, such as described above, the ultrasonic assembly UA being mounted on a catheter. The focus control unit FCU includes electronic components generating an electric control signal CS to the device D so as to apply voltages to control the one or more fluid focus lenses in the ultrasonic assembly UA based on a user input. The focus control unit translates a user input to the appropriate control signals CS to produce a desired ultrasonic focus pattern with the specific configuration of one or more fluid focus lenses in the ultrasonic assembly UA. The user may select one of a predefined set of focus patterns, or the user may adjust a knob, a trackball, a joystick or the like to influence the focus pattern during treatment. Further, the focus control unit FCU generates an electric ultrasonic signal US to the ultrasonic transducer in the ultrasonic assembly UA, and thus the ultrasonic power or intensity may be adjustable by the user during treatment. The control electronics is preferably designed to receive external signals to halt to adjust the therapeutic intervention. This adjustment may include control of the power, frequency (for spatial control), or amplitude of the acoustic pressure field. The external signal can be generated in response to real-time monitoring of the treatment or from a previously designed therapy plan.

Certain specific details of the disclosed embodiment are set forth for purposes of explanation rather than limitation, so as to provide a clear and thorough understanding of the present invention. However, it should be understood by those skilled in this art, that the present invention might be practiced in other embodiments that do not conform exactly to the details set forth herein, without departing significantly from the spirit and scope of this disclosure. Further, in this context, and for the purposes of brevity and clarity, detailed descriptions of well-known apparatuses, circuits and methodologies have been omitted so as to avoid unnecessary detail and possible confusion.

To sum up: the invention provides an ultrasonic assembly suited for attachment to a catheter, e.g. for medical treatment. The ultrasonic assembly includes an adjustable ultrasonic focus mechanism arranged in connection with the ultrasonic transducer to adjust focus of ultrasonic waves generated by the transducer. The ultrasonic focus mechanism includes a fluid focus lens with at least two fluids separated by an interface such that ultrasonic waves are substantially reflected at the interface. At least two electrodes are arranged in connection with the fluid focus lens so as to allow adjustment of the interface shape, e.g. a curvature of the interface, when a voltage is applied to the electrodes. In preferred embodiments the electrodes are arranged so as to allow adjustment of the fluid focus lens in an elevation direction as well as in a radial direction. In simple embodiments with rotational symmetric geometry with the transducer positioned in the centre of the fluid focus lens, ultrasonic waves can be focused in an annular ring. This is e.g. suitable for ablative or coagulative necrotic treatment of human tissue, e.g. for atrial fibrillation treatment. In some embodiments, the assembly has a number of separate individually adjustable fluid focus lens compartments allowing a more detailed control of the ultrasonic focus pattern.

Reference signs are included in the claims, however the inclusion of the reference signs is only for clarity reasons and should not be construed as limiting the scope of the claims.

The invention claimed is:
1. An ultrasonic assembly arranged for attachment to an associated catheter (C), the ultrasonic assembly including:
an ultrasonic transducer (T) arranged for attachment on a distal end of the catheter (C), and
an adjustable ultrasonic focus mechanism arranged in connection with the ultrasonic transducer (T), the mechanism being arranged to adjust focus of ultrasonic waves generated by the transducer, the adjustable ultrasonic focus mechanism including
a fluid focus lens including a first fluid (F1) arranged with an interface (I) to a second fluid (F2) providing an ultrasonic reflection at the interface (I), and
first and second electrodes (E, E1, E2) arranged in connection with the fluid focus lens so as to allow adjustment of a shape of the interface (I) upon application of an electric voltage (VS) to the first and second electrodes (E, E1, E2).

2. Ultrasonic assembly according to claim 1, wherein the first and second electrodes (E, E1, E2) are arranged so as to allow adjustment of the fluid focus lens in an elevation direction (D-e).

3. Ultrasonic assembly according to claim 1, wherein the first and second electrodes (E, E1, E2) adjust the fluid focus lens in a radial direction (D-r).

4. Ultrasonic assembly according to claim 3, wherein the ultrasonic transducer (T) generates ultrasonic waves in a radial pattern.

5. Ultrasonic assembly according to claim 4, wherein the first fluid (F1) of the fluid focus lens has a rotationally symmetric shape around an axis, wherein the ultrasonic transducer (T) is positioned on the axis in contact with the first fluid (F1), and wherein the interface (I) to the second fluid (F2) is adjustable in its curvature, so as to allow a focused ultrasonic beam in an annular ring (CRF) centered around the axis.

6. Ultrasonic assembly according to claim 1, wherein the interface (I) has a spherical shape, and wherein the first and second electrodes (E, E1, E2) are arranged so as to allow adjustment of a curvature of the interface (I).

7. Ultrasonic assembly according to claim 1, wherein the first fluid (F1) provides a substantially linear curvature.

8. Ultrasonic assembly according to claim 1, wherein the first fluid (F1) is one of: water, and oil.

9. Ultrasonic assembly according to claim 8, wherein the second fluid (F2) is one of: air, mercury, a gallium-indium alloy.

10. Ultrasonic assembly according to claim 1, wherein the adjustable ultrasonic focus mechanism includes a plurality of radially adjacent fluid focus lenses (S1, S2, S3, S4, S5, S6) each including first and second fluids (F1, F2) and at least two electrodes arranged so as to allow individual adjustment of the plurality of fluid focus lenses (S1, S2, S3, S4, S5, S6).

11. Ultrasonic assembly according to claim 10, wherein the plurality of fluid focus lenses (S1, S2, S3, S4, S5, S6) are arranged to form a body with rotational symmetric shape around an axis.

12. Ultrasonic assembly according to claim 11, wherein the plurality of fluid focus lenses (S1, S2, S3, S4, S5, S6) are arranged so as to allow a focused ultrasonic beam in an annular ring with a center away from the axis (DF).

13. Ultrasonic assembly according to claim 1, wherein the ultrasonic transducer (T) is arranged to generate ultrasound power allowing ablative or coagulative necrotic treatment of human tissue.

14. Ultrasonic ablative device (D) including a catheter (C) attached to the ultrasonic assembly of claim 1.

15. Ultrasonic ablative system including an ultrasonic ablative device (D) according to claim 14, and a focus control unit (FCU) electrically connected to the first and second electrodes of the ultrasonic assembly (UA).

* * * * *